(12) United States Patent
Kirts et al.

(10) Patent No.: US 6,397,665 B1
(45) Date of Patent: Jun. 4, 2002

(54) APPARATUS FOR DETECTING AND MEASURING FOAM FORMING COMPOUNDS IN AQUEOUS SOLUTIONS

(75) Inventors: Richard Eugene Kirts; Brad Lee Hollan, both of Oxnard, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/566,888

(22) Filed: May 8, 2000

(51) Int. Cl.[7] .......................... G01N 24/00; G01N 3/32
(52) U.S. Cl. .......................... 73/60.11; 73/579; 73/592
(58) Field of Search .......................... 73/60.11, 61.41, 73/64.41, 64.43, 592, 579

(56) References Cited

U.S. PATENT DOCUMENTS

| | | | |
|---|---|---|---|
| 3,151,061 A | * | 9/1964 | Orr .......................... 73/60.11 |
| 5,465,610 A | * | 11/1995 | Loisel .......................... 73/60.11 |
| 5,597,950 A | * | 1/1997 | Mullen .......................... 73/60.11 |

FOREIGN PATENT DOCUMENTS

| | | | | |
|---|---|---|---|---|
| DE | 4036344 | * | 5/1992 | .......................... 73/60.11 |
| SU | 1302193 | * | 4/1987 | .......................... 73/60.11 |
| SU | 1520400 | * | 11/1989 | .......................... 73/60.11 |

* cited by examiner

*Primary Examiner*—Daniel S. Larkin
(74) *Attorney, Agent, or Firm*—David Kalmbaugh (57) ABSTRACT

An apparatus for detecting change in the foam forming characteristic of an input stream of an aqueous solution which continuously samples the input stream by taking a series of discrete, independent measurements. A sample of the input stream is collected, analyzed, then discarded. The collect-analyze-discard cycle is repeated. The apparatus relies on an acoustic sensor to measure foam height within a column. This allows the column containing the foam to be fabricated from any material, including durable plastics. A sample of the input stream is introduced into the apparatus. The sample is then aerated by an aeration stone to produce foam. The height of the column of foam produced is then measured using the acoustic sensor. The sample is then discarded and the process repeated. The height of the foam column is correlated with the concentration of foam forming chemical.

21 Claims, 5 Drawing Sheets

APPARATUS FOR DETECTING AND MEASURING FOAM FORMING COMPOUNDS IN AQUEOUS SOLUTIONS

BACKGROUND OF THE INVENTION

1. Field of the Invention

The present invention relates generally to an apparatus for detecting the presence of foam forming compounds in aqueous solutions. More particularly, the present invention relates to an apparatus which detects the presence of specific foam forming compounds in an aqueous solution and, when calibrated, measures the concentration form forming compounds in the solution.

2. Description of the Prior Art

Foam forming compounds include cleaning compounds such as detergents, fire-fighting chemicals, and naturally occurring surfactants such as plant extractives. The presence of foam forming compounds can interfere with the operation of chemical plants, such as wastewater treatment plants, by causing inaccurate readings in flow and level sensing devices.

Foaming of wastewater tends to lift solid materials out of the liquid phase and suspend them in the foam. These solid materials may include metals or other hazardous materials. In open top tanks, pollutant-laden foams may be blown off the surface of the wastewater and onto the surrounding property. Hazards of this type often result in citations from public health offices and environmental protection officials.

Some foam forming chemical are toxic to the microorganisms used in wastewater treatment plants. Early detection of foam forming chemicals permits process streams contaminated with these chemicals to be diverted from the main process flow. The diverted flow can be subsequently treated in a specialized forming agent removal process.

Devices used in the past to detect the presence of foam forming chemicals cannot rapidly detect a change of state from a foaming input stream to a non-foaming input stream. For example, if a prior art device was measuring the foam forming characteristic of an input stream that contained a high concentration of a foam forming chemical, and then the input stream was changed to a stream that contained little or no foam forming chemical, the prior art device could not rapidly detect the change in input stream composition. This is because the prior art device has a fixed or static solution reservoir at the bottom of the device, and the concentration of the foam forming chemical in that reservoir is changed only by dilution from the input stream. It may take several minutes before the solution in the reservoir has been diluted by a low concentration input stream to a concentration that no longer forms a significant amount of foam.

Devices used in the past to detect the presence of foam forming chemicals are generally not automated. These devices are manually operated and best suited to a laboratory environment.

Prior art devices for detecting the presence of foam forming chemicals are also fragile, generally consisting of a piece of custom blown glasswork.

In addition, prior art devices rely on photo-optical sensor pairs to detect and measure the presence of foam at discrete locations. This approach is expensive to implement and provides a limited number of foam height detection values. Also, reliance upon photo-optical pairs to detect the present of foam requires that the column containing the foam be transparent. In some foam sensing applications, a film of oil, algae, bacteria, and other deposits may eventually occlude a clear column. This renders the photo-optical sensors inoperable.

Further, at low concentrations of foam forming chemical the foam can usually be characterized as being composed of a small number of large bubbles. The beam from a photo-optical sensor can intermittently pass through such loosely structured foam, resulting in intermittent false readings of foam height.

SUMMARY OF THE INVENTION

A sample of the liquid to be tested enters the apparatus comprising the present invention through a fill valve at the top of a tubular column, flows down the sides of the column, and collects in a lower portion of the column. The liquid level in the column rises to the level of an outlet port. Excess liquid flows out of the column through a chamber exiting the apparatus through a discharge port.

After a sample of liquid has collected in the lower portion of the column, an air pump is actuated and compressed air flows into the sample through an aeration stone. The air bubbles produced by the aeration stone cause the foam forming compounds in the sample to produce foam. The foam rises in the column and lifts a float which functions as a solid target for an ultrasonic distance measuring device. The measuring device measures the height of the foam within the column generating a continuous analog electrical output signal which is a function of foam height. The value of voltage produced by the measuring device is measured and retained by a sample-and-hold circuit connected to the measuring device.

After a foam height measurement has been made, the fill valve closes, an sample drain valve opens, and a three-way valve is positioned to divert the compressed air from the aeration stone to the top of the column. This forces the sample of solution and foam from the column through a drain valve. After the solution has been drained from the column, the fill valve opens, the drain valve closes, air is re-directed to the aeration stone, and the entire sample acquisition and measurement cycle is repeated.

DETAILED DESCRIPTION OF THE PREFERRED EMBODIMENT

Figure 1:
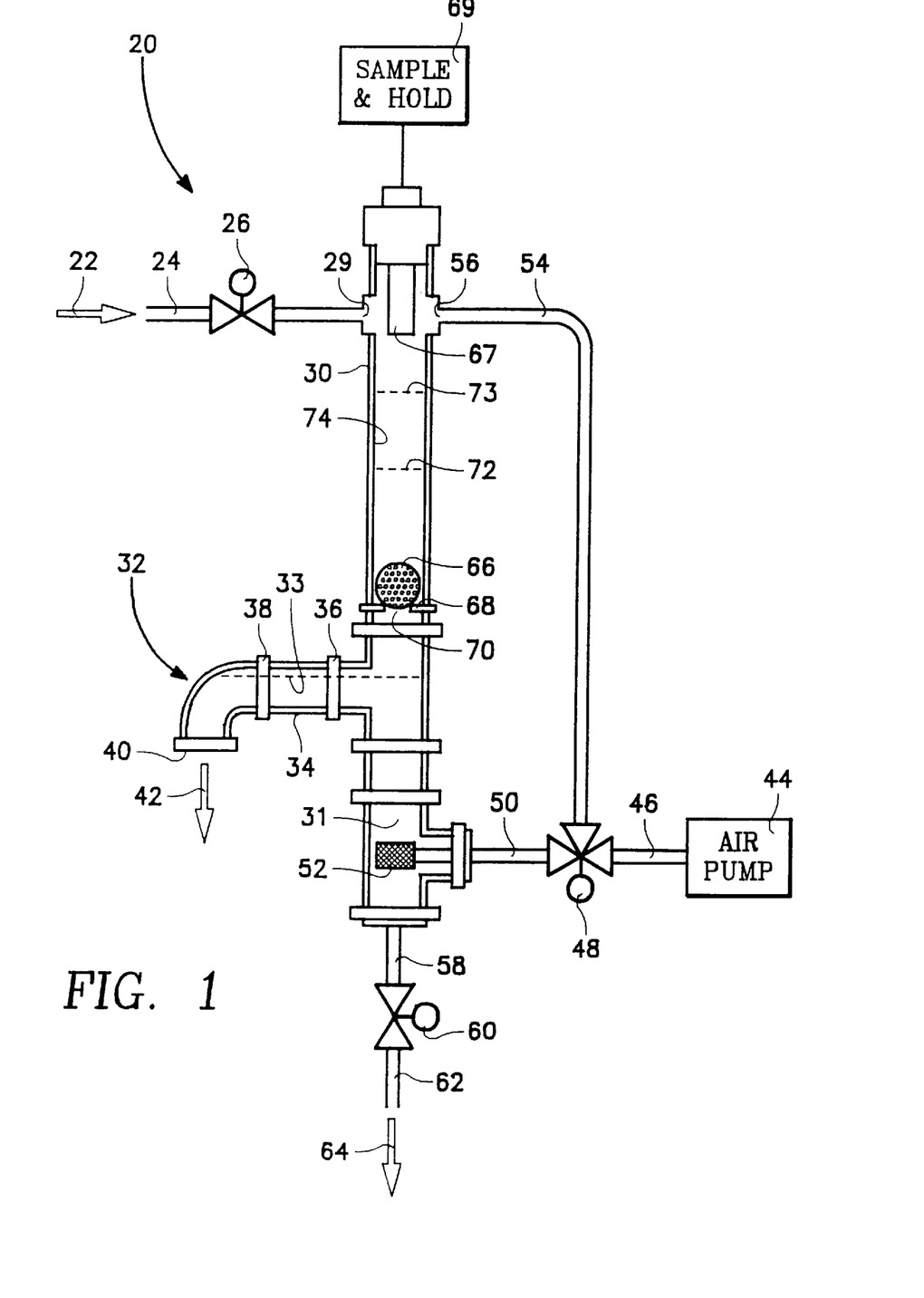
FIG. 1 is a plan view of an apparatus for detecting and measuring foam forming compounds in aqueous solutions comprising the present invention.

Referring first to FIG. 1, there is shown an apparatus, designated generally by the reference numeral 20, which measures the foam foaming capability of the solution with a time series of discrete tests. The apparatus 20 has detected fewer than ten parts per million of aqueous fire fighting foam (AFFF) in less than thirty seconds.

A sample of a liquid to be tested enters apparatus 20 (as indicated by arrow 22) through an inlet pipe 24 which includes an electrically operated fill valve 26. When valve 26 is electrically de-activated, fill valve 26 is open allowing the liquid to pass through inlet pipe 24 and an opening 29 at the top of a tubular column 30 into tubular column 30. The liquid then flows down the sides of tubular column 30, and collects in the bottom or lower portion 31 of tubular column 30.

The liquid level in the column rises to the level of an outlet port, which is designated generally by the reference numeral 32. Outlet port 32 includes a chamber 34 and a pair of pair of weirs 36 and 38 positioned at each end of chamber 34. Excess liquid flows out through chamber 34 from the lower portion 31 of tubular column 30. The excess liquid then exits outlet port 32 through an opening/discharge port 40 (as indicated by arrow 42). The weirs 36 and 38 at each end of chamber 34 control the rate of outflow of excess liquid and dampen oscillations in foam column height. Dashed line 33 indicates the height of weirs 36 and 38 within chamber 34.

After a sample of the liquid has collected in the lower portion 31 of column tubular 30, an electrically operated air pump 44 is actuated providing compressed air which flows through a pipe 46, a three-way electrically operated air valve 48, and a pipe 50 into the sample through aeration stone 52. The many small air bubbles produced by aeration stone 52 cause the foam forming compounds in the sample to produce foam. The foam rises in tubular column 30 lifting a spherical shaped lightweight float/target 66 into the upper portion of tubular column 30.

When apparatus 20 is not operational, float 66 rests on a support member 68 located within tubular column 30. Support member 68 has a centrally located opening 70 which allows foam to pass through support member 68 lifting float 66 into the upper portion of tubular column 30.

The float 68 serves as a solid target for an ultrasonic distance measuring device 67. The ultrasonic distance measuring device 67, which is positioned at the top of tubular column 30, measures the height the column of foam and target 66 rises to within tubular column 30. The ultrasonic distance measuring device 67 produces a continuous analog electrical output signal which is a function of foam height within tubular column 30. The output signal's voltage value produced by the ultrasonic distance measuring device 67 is measured, sampled, and retained by a sample-and-hold circuit 69 connected to measuring device 67.

At this time it should be noted that a laser distance-measuring device could be substituted for the ultrasonic distance measuring device 67 to perform the function of measuring the height of the foam column within tubular column 30.

After a foam height measurement within tubular column 30 has been made, fill valve 26 closes and an electrically operated sample drain valve 60 opens. When electrically deactivated, drain valve 60, which is connected to the bottom of tubular column 30 by a pipe 58, allows liquid in tubular column 30 to exit tubular column 30 via connecting pipe 58 and a drain pipe 62 (as indicated by arrow 64).

Simultaneously, three way electrically operated air valve 48 is positioned to divert the compressed air from the aeration stone 52 to the top of column 30 via a connecting air pipe 54 through an opening 56 at the top of column 30. This diversion of compressed air forces the sample of solution and foam out of tubular column 30 through drain valve 62 and drain pipe 64.

After the solution and foam have been drained from tubular column 30, valve 26 opens, valve 60 closes, and three-way air valve 48 redirects air to the aeration stone 52. The entire sample acquisition and measurement cycle is repeated.

If the height of the column of foam rises too high in tubular column 30, valve 26 is temporarily closed until the next drain cycle. Closing valve 26 precludes the introduction of excessive amounts of foam forming chemicals.

Figure 3A:
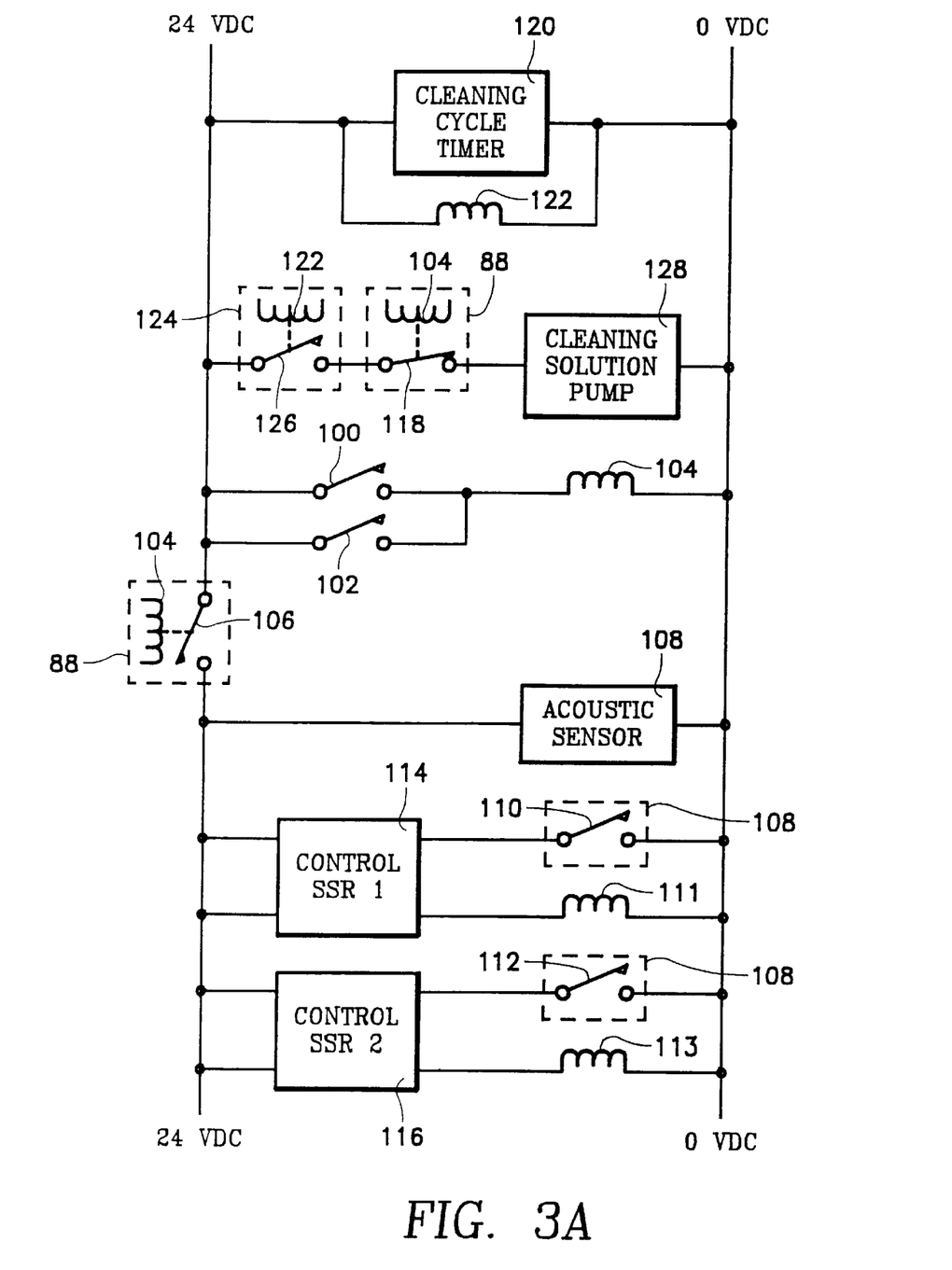
FIGS. 3A and 3B are an electrical schematic diagram of the 24 VDC control circuity for the apparatus of FIG. 1.

The accumulation of deposits of organic matter on the inside wall 74 of tubular column 30 may interfere with the free movement of the float/target 66. To preclude the growth of algae and bacterial mats on the inside wall 74 of column 30 and remove deposits of oil and grease from the inside wall 74 of column 30, apparatus 20 includes a cleaning cycle timer 120 (FIG. 3A) that allows for periodic flushing of the wall 74 of the column 30 with a biocide cleaning solution. The cleaning solution may be a solution of sodium hypochlorite or potassium permanganate. A cleaning solution pump 128 is activated periodically (about once a day) for a brief time period to flow the biocide cleaning solution over the wall 74 of column 30. Energizing coil 122 of cleaning cycle timer 120 closes normally open contact 126 of relay 124 activating cleaning solution pump 128 whenever contact 118 of relay 88 is in the closed position, as shown in FIG. 3A.

Referring now to FIGS. 1, 2, 3A, and 3B, a relay logic circuit controls the apparatus 20 in a typical process application. Included in the relay logic circuit is a latching relay 92 which is set when the foam height exceeds an input upper set point 73. The relay 92 remains latched until the height of the foam column falls below an input lower set point 72 and remains below lower set point 72 for a time period set by a time delay relay 138.

The latching relay 92 is used to control a process, such as diverting a contaminated flow stream from a wastewater treatment plant to storage tanks or a specialized treatment processing facility via diverter valve 96.

Figure 2:
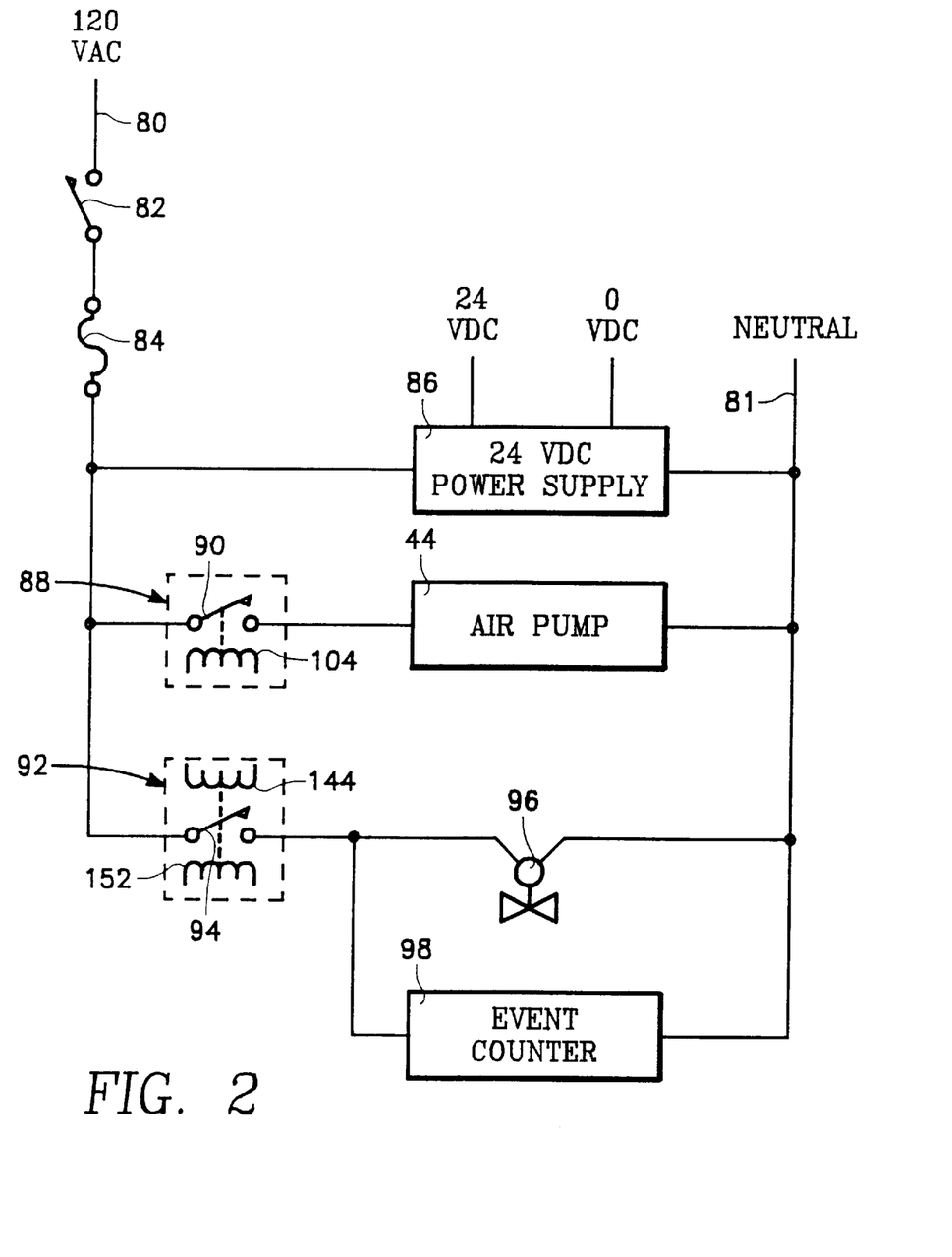
FIG. 2 is an electrical schematic diagram of the 120 VAC control circuity for the apparatus of FIG. 1.

The 120 VAC control circuity of FIG. 2 includes a 120 VAC power line 80, a neutral power line 81, a manual power switch 82 within power line 80 and a fuse 84 connected to switch 82. Closure of switch 82 supplies 120 VAC to a 24 VDC power supply 86 which provides 24 VDC to the electrical components of FIGS. 3A and 3B.

When normally open contact 90 of relay 88 is closed 120 VAC is supplied to air pump 44 activating air pump 44. Further, when normally open contact 94 of latching relay 92 is closed 120 VAC is also supplied to diverter valve 96 and an event counter 98. The event counter 98 counts the number of times the concentration of foam producing chemicals in the wastewater has exceeded the set points 72 and 73 of apparatus 20.

Figure 3B:
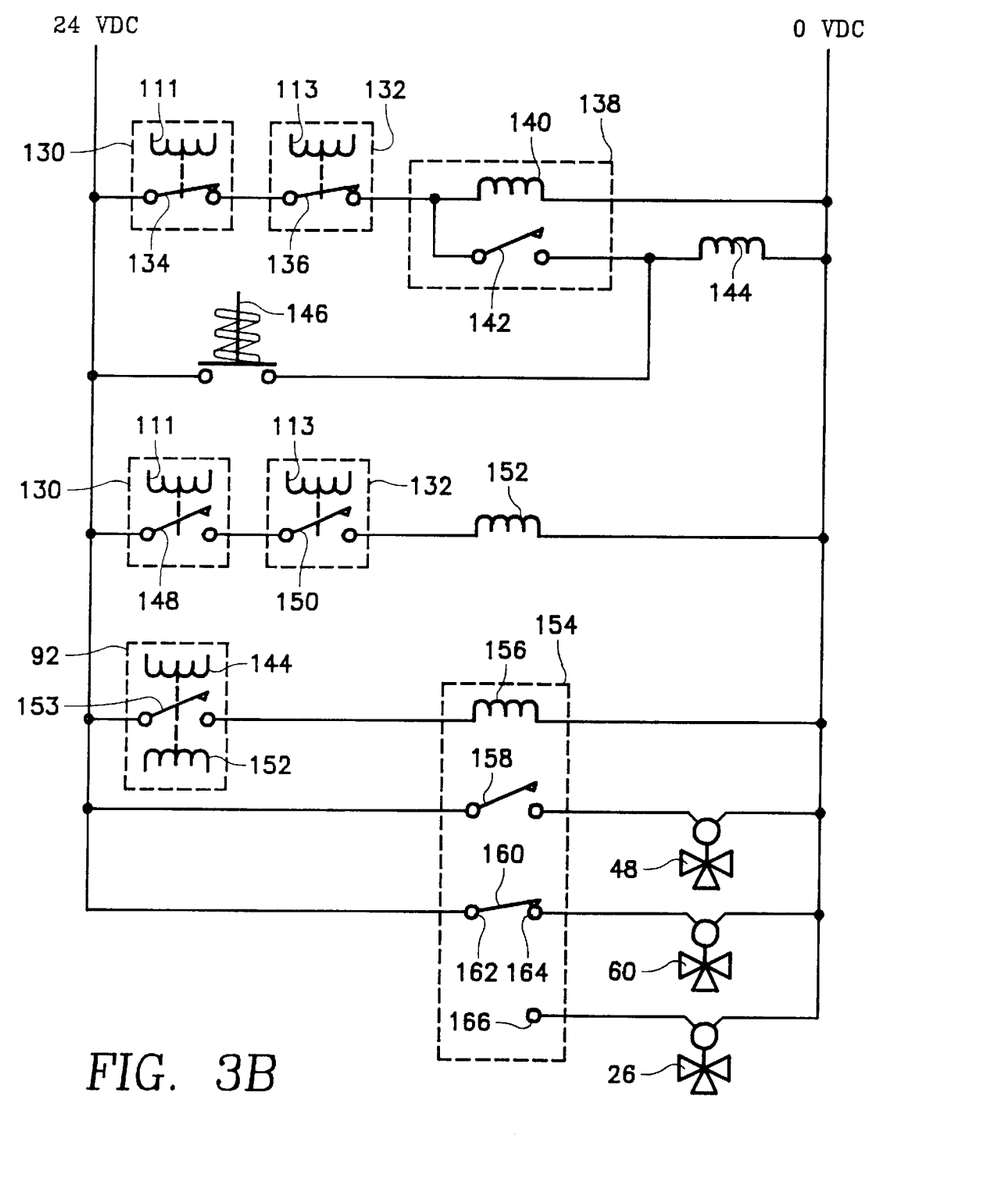

When a sample is diverted from the contaminated flow stream, normally open contact 100 of a flow switch (not illustrated) closes supplying 24 VDC to a relay coil 104 energizing coil 104. Energizing coil 104 closes contact 90 of relay 88 activating air pump 44 which then supplies compressed air to tubular column 30. Energizing coil 104 also closes normally open contact 106 of relay 88 supplying 24 VDC to control solid state relay 114, control solid state relay 116, and acoustic sensor 108. Relays 114 and 116 operate to increase supply current respectively to coils 111 and 113 to activate coils 111 and 113 when normally open contacts 110 and 112 of acoustic sensor 108 are closed.

When spherical shaped lightweight float/target 66, which is being lifted by a column of foam, reaches lower set point 72, normally open contact 110 of acoustic sensor 108 closes which energizes coil 111 of relay 130. Energizing coil 111 closes normally open contact 148 of relay 130. When spherical shaped lightweight float/target 66 reaches upper set point 73, normally open contact 112 of acoustic sensor 108 closes which energizes coil 113 of relay 132. Energizing coil 113 closes normally open contact 150 of relay 132. Closing contact 150 supplies 24 VDC to the latch coil 152 of latch relay 92 which results in the closure of contact 94 of latch relay 92. Closing contact 94 of latch relay 92 activates diverter valve 96 and event counter 98.

Energizing coil 111 of relay 130 opens normally closed contact 134 of relay 130. Similarly, energizing coil 113 of relay 132 opens normally closed contact 136 of relay 132. This insures that the unlatch coil 144 of latch relay 92 is not energized.

When spherical shaped lightweight float/target 66 drops below upper set point 73, normally open contact 112 of acoustic sensor 108 opens which de-energizes coil 113 of relay 132. De-energizing coil 113 of relay 132 closes contact 136 of relay 132. When spherical shaped lightweight float/target 66 drops below lower set point 72, normally open contact 110 of acoustic sensor 108 opens which de-energizes coil 111 of relay 130. De-energizing coil 111 of relay 130 closes contact 134 of relay 130, resulting in 24 VDC being supplied to the coil 140 of a time delay relay 138. After a time delay of 120 seconds, contact 142 closes supplying 24 VDC to the unlatch coil 144 of latch relay 92. Energizing the unlatch coil 144 of latch relay 92 opens contact 94 of latch relay 92. The unlatch coil 144 of latch relay 92 is also energized by depressing momentary contact switch 146.

Latch relay 92 is also connected to a blow down timer 154. When latch coil 152 of latch relay 92 is energized, contact 153 of latch relay 92 closes supplying 24 VDC to the coil 156 of a blow down timer 154. This closes normally open contact 158 of timer 154 resulting in 24 VDC being supplied to air valve 48. Energizing air valve 48 diverts compressed air through pipe 54 to the top of column 30 to force foam and the wastewater sample through valve 60 and drain pipe 62. Energizing coil 156 of a blow down timer 154 also moves two position contact 160 such that contact 160 opens the current path between terminal 162 and terminal 164 and closes the current path between terminals 162 and 166. This results in fill valve 26 being electrically activated. Activating fill valve 26 shuts off the flow of liquid through inlet pipe 24 and opening 29 at the top of tubular column 30 into tubular column 30.

When coil 156 of blow down timer 154 is energized, contact 160 opens de-energizing drain valve 60. De-energizing drain valve 60 results in the foam and wastewater sample exiting tubular column 30 through pipe 58, drain valve 60, and drain pipe 62.

When the unlatch coil 144 of relay 92 is energized contact 153 opens de-energizing coil 156 of blow down timer 154. This results in contact 158 opening de-activating valve 48 which then diverts air flow through valve 48 and pipe 52 to aeration stone 52. Activating valve 48 directs air through pipe 54 to the top of tubular column 30 so that the foam and wastewater within tubular column 30 is blown out of tubular column 30.

Further, contact 160 returns to the position illustrated in FIG. 3B completing a current path between terminals 162 and 164 which activates drain valve 60 blocking the flow of wastewater and foam out of tubular column 30 through pipe 58 and drain valve 60.

At this time it should be noted that the 24 VDC control circuit of FIGS. 3A and 3B includes a manual switch which has a normally open contact 102. When the manual switch is activated closing contact 102 the circuit of FIGS. 3A and 3B operate in exactly the same manner as when contact 100 closes. The purpose of this switch is to provide the capability to manually unlatch relay 92 and reposition valve 96.

It should be noted that the apparatus 20 is fabricated primarily from durable plastic allowing for a long life span. It should also be noted that a sample from the input stream may be collected, analyzed, and then discarded in about two minutes. This results in any error which occurs in measuring the change in composition of the input stream being no larger than the period required for the collect-analyze-discard cycle of about two minutes.

Figure 4:
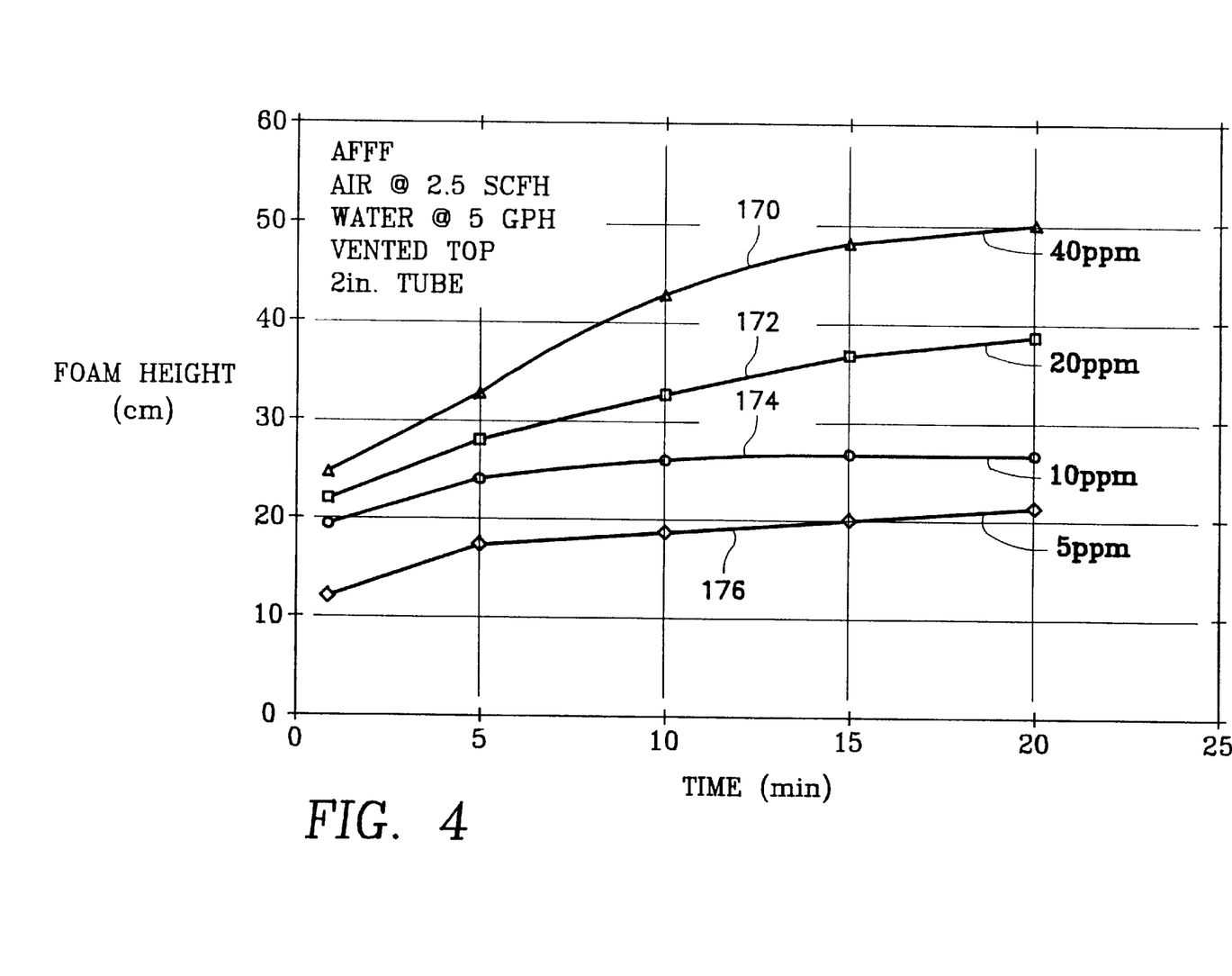
FIG. 4 illustrates a series of plots which depict foam height as a function of time for solutions of aqueous fire fighting foam.

Referring to FIG. 4, FIG. 4 illustrates four plots 170, 172, 174, and 176 in which foam height is depicted as a function of time for aqueous fire fighting foam (AFFF) having 40 ppm (plot 170), 20 ppm (plot 172), 10 ppm (plot 174), and 5 ppm (plot 176) for apparatus 20.

From the foregoing, it may readily be seen that the present invention comprises a new, unique, and exceedingly useful system for detecting and measuring foam forming compounds in aqueous solutions which constitutes a considerable improvement over the known prior art. Many modifications and variations of the present invention are possible in light of the above teachings. It is to be understood that within the scope of the appended claims the invention may be practiced otherwise than as specifically described.

What is claimed is:

1. An apparatus for detecting and measuring foam in wastewater, comprising:

a vertically positioned tubular column having an inner wall, said tubular column having first and second openings disposed within an upper portion of said tubular column;

a first valve means having an inlet port for receiving said wastewater and an outlet port connected to the first opening of said tubular column, said first valve means when opened allowing said wastewater to pass through the first opening of said tubular column and flow down the inner wall of said tubular column to a lower portion of said tubular column;

air supply means for generating compressed air;

second valve means having an inlet port connected to said air supply means to receive said compressed air, a first outlet port connected to the second opening of said tubular column, and a second outlet port, said second valve means diverting said compressed air through the first outlet port thereof and the second opening of said tubular column into said tubular column when said second valve means is activated, said valve means directing said compressed air through the second outlet port thereof when said second valve means is de-activated;

third valve means having an inlet port connected to the lower portion of said tubular column and an outlet port for draining said wastewater from said tubular column;

an aeration stone positioned in the lower portion of said tubular column, said aeration stone having an inlet port connected to the second outlet port of said second valve means to receive said compressed air directed through the second outlet port of said second valve means;

control means connected to said first valve means, said second valve means, and said third valve means;

said control means opening said first valve means allowing said wastewater to pass through said first valve means into said tubular column;

said control means de-activating said second valve means allowing said compressed air to flow through the second outlet port of said valve means to said aeration stone;

said aeration stone, responsive to said compressed air, generating air bubbles within said wastewater resulting in a formation of said foam within said tubular column above said wastewater;

a spherical shaped float positioned above the lower portion of said tubular column, said foam raising said spherical shaped float within said tubular column;

measuring means for measuring the height said spherical shaped float rises to within said tubular column, said measuring means producing a continuous analog electrical output signal indicative of foam height within said tubular column;

said control means simultaneously activating said second valve means and opening said third valve means diverting said compressed air from said aeration stone to said upper portion of said tubular column forcing said wastewater and said foam out of said tubular column through said third valve means.

2. The apparatus of claim 1 wherein said first valve means comprises a fill valve.

3. The apparatus of claim 1 wherein said second valve means comprises a three-way valve.

4. The apparatus of claim 1 wherein said third valve means comprises a drain valve.

5. The apparatus of claim 1 further comprising an air pipe having one end connected to the first outlet port of said second valve means and the opposite end connected to the second opening of said tubular column.

6. The apparatus of claim 1 further comprising a sample and hold circuit connected to said measuring means to sample and retain said continuous analog electrical output signal produced by said measuring means.

7. The apparatus of claim 1 further comprising a drain pipe having one end connected to the outlet port of said third valve means.

8. The apparatus of claim 1 wherein said control means comprises:

a twenty-four volt power supply having an output;

a latching relay having a normally open contact, the normally open contact of said latching relay having an input terminal connected to the output of said twenty-four volt power supply and an output terminal; and a timer having a coil connected to the output terminal of the normally open contact of said latching relay;

said timer having a normally open contact, the normally open contact of said timer having an input terminal connected to the output of said twenty-four volt power supply and an output terminal connected to said second valve means; and said timer having a two position contact, the two position contact of said timer having an input terminal connected to the output of said twenty-four volt power supply, a first output terminal connected to said third valve means, and a second output terminal connected go said first valve means.

9. The apparatus of claim 1 further comprising a discharge port positioned above the lower portion of said tubular column, said discharge port being coupled to said tubular column, said discharge port draining said wastewater which is excess from said tubular column.

10. The apparatus of claim 9 wherein said discharge port includes a chamber having a pair of weirs, one of said pair of weirs being positioned at one end of said chamber and the other of said pair of weirs being positioned at the opposite end of said chamber.

11. An apparatus for detecting and measuring foam in wastewater, comprising:

a vertically positioned tubular column having an inner wall, said tubular column having first and second openings disposed within an upper portion of said tubular column;

a fill valve having an inlet port for receiving said wastewater and an outlet port connected to the first opening of said tubular column, said fill valve when opened allowing said wastewater to pass through the first opening of said tubular column and flow down the inner wall of said tubular column to a lower portion of said tubular column;

an air pump having an outlet port for providing compressed air;

a three-way valve having an inlet port connected to the outlet port of said air pump to receive said compressed air, a first outlet port connected to the second opening of said tubular column, and a second outlet port, said three-way valve when activated diverting said compressed air through the first outlet port thereof and the second opening of said tubular column into said tubular column, said three-way valve when de-activated directing said compressed air through the second outlet port thereof;

an aeration stone positioned in the lower portion of said tubular column, said aeration stone having an inlet port connected to the second outlet port of said three-way valve to receive said compressed air directed through the second outlet port of said three-way valve;

a drain valve having an inlet port connected to the lower portion of said tubular column and an outlet port;

a control circuit connected to said fill valve, said three-way valve, and said drain valve;

said control circuit first opening said fill valve allowing said wastewater to pass through said fill valve into said tubular column;

said control circuit next de-activating said three-way valve allowing said compressed air to flow through the second outlet port of said three-way valve to said aeration stone;

said aeration stone, responsive to said compressed air, generating air bubbles within said wastewater resulting in a formation of said foam within said tubular column above said wastewater;

a spherical shaped float positioned above the lower portion of said tubular column, said foam raising said spherical shaped float within said tubular column;

an ultrasonic distance measuring device mounted at an upper end of said tubular column and extending into said tubular column;

said ultrasonic distance measuring device measuring the height said spherical shaped float rises to within said tubular column, said ultrasonic distance measuring device producing a continuous analog electrical output signal indicative of foam height within said tubular column;

said control circuit simultaneously activating said three-way valve and opening said drain valve diverting said compressed air from said aeration stone to said upper portion of said tubular column forcing said wastewater and said foam out of said tubular column through said drain valve.

12. The apparatus of claim 11 further comprising an air pipe having one end connected to the first outlet port of said three-way valve and the opposite end connected to the second opening of said tubular column.

13. The apparatus of claim 11 further comprising a sample and hold circuit connected to said ultrasonic distance measuring device to sample and retain said continuous analog electrical output signal produced by said ultrasonic distance measuring device.

14. The apparatus of claim 11 further comprising a drain pipe having one end connected to the outlet port of said drain valve.

15. The apparatus of claim 11 wherein said control circuit comprises:
- a twenty-four volt power supply having an output;
- a latching relay having a normally open contact, the normally open contact of said latching relay having an input terminal connected to the output of said twenty-four volt power supply and an output terminal; and
- a timer having a coil connected to the output terminal of the normally open contact of said latching relay;
- said timer having a normally open contact, the normally open contact of said timer having an input terminal connected to the output of said twenty-four volt power supply and an output terminal connected to said three-way valve; and
- said timer having a two position contact, the two position contact of said timer having an input terminal connected to the output of said twenty-four volt power supply, a first output terminal connected to said drain valve, and a second output terminal connected to said fill valve.

16. The apparatus of claim 11 further comprising a discharge port positioned above the lower portion of said tubular column, said discharge port being coupled to said tubular column, said discharge port draining said wastewater which is excess from said tubular column.

17. The apparatus of claim 16 wherein said discharge port includes a chamber having a pair of weirs, one of said pair of weirs being positioned at one end of said chamber and the other of said pair of weirs being positioned at the opposite end of said chamber.

18. An apparatus for detecting and measuring foam in wastewater, comprising:
- a vertically positioned tubular column having an inner wall, said tubular column having first and second openings disposed within an upper portion of said tubular column;
- a fill valve having an inlet port for receiving said wastewater and an outlet port connected to the first opening of said tubular column, said fill valve when opened allowing said wastewater to pass through the first opening of said tubular column and flow down the inner wall of said tubular column to a lower portion of said tubular column;
- an air pump having an outlet port for providing compressed air;
- a three-way valve having an inlet port connected to the outlet port of said air pump to receive said compressed air, a first outlet port, and a second outlet port, said three-way valve when activated diverting said compressed air through the first outlet port thereof and the second opening of said tubular column into said tubular column, said three-way valve when de-activated directing said compressed air through the second outlet port thereof;
- an air pipe having one end connected to the first outlet port of said three-way valve and the opposite end connected to the second opening of said tubular column;
- an aeration stone positioned in the lower portion of said tubular column, said aeration stone having an inlet port connected to the second outlet port of said three-way valve to receive said compressed air directed through the second outlet port of said three-way valve;
- a drain valve having an inlet port connected to the lower portion of said tubular column and an outlet port;
- a control circuit connected to said fill valve, said three-way valve, and said drain valve;
- said control circuit first opening said fill valve allowing said wastewater to pass through said fill valve into said tubular column;
- said control circuit next de-activating said three-way valve allowing said compressed air to flow through the second outlet port of said three-way valve to said aeration stone;
- said aeration stone, responsive to said compressed air, generating air bubbles within said wastewater resulting in a formation of said foam within said tubular column above said wastewater;
- a spherical shaped float positioned above the lower portion of said tubular column, said foam raising said spherical shaped float within said tubular column;
- an ultrasonic distance measuring device mounted at an upper end of said tubular column and extending into said tubular column;
- said ultrasonic distance measuring device measuring the height said spherical shaped float rises to within said tubular column, said ultrasonic distance measuring device producing a continuous analog electrical output signal indicative of foam height within said tubular column;
- said control circuit simultaneously activating said three-way valve and opening said drain valve diverting said compressed air from said aeration stone to said upper portion of said tubular column forcing said wastewater and said foam out of said tubular column through said drain valve;
- a sample and hold circuit connected to said ultrasonic distance measuring device to sample and retain said continuous analog electrical output signal produced by said ultrasonic distance measuring device.

19. The apparatus of claim 18 further comprising a drain pipe having one end connected to the outlet port of said drain valve.

20. The apparatus of claim 18 wherein said control circuit comprises:
- a twenty-four volt power supply having an output;
- a latching relay having a normally open contact, the normally open contact of said latching relay having an input terminal connected to the output of said twenty-four volt power supply and an output terminal; and
- a timer having a coil connected to the output terminal of the normally open contact of said latching relay;
- said timer having a normally open contact, the normally open contact of said timer having an input terminal connected to the output of said twenty-four volt power supply and an output terminal connected to said three-way valve; and
- said timer having a two position contact, the two position contact of said timer having an input terminal connected to the output of said twenty-four volt power supply, a first output terminal connected to said drain valve, and a second output terminal connected to said fill valve.

21. The apparatus of claim 18 further comprising a discharge port positioned above the lower portion of said tubular column, said discharge port being coupled to said tubular column, said discharge port draining said wastewater which is excess from said tubular column.

* * * * *